United States Patent [19]

Patroni

[11] Patent Number: 4,966,963

[45] Date of Patent: * Oct. 30, 1990

[54] PRODUCTION OF PROTEINS IN ACTIVE FORMS

[75] Inventor: Joseph J. Patroni, West Preston, Australia

[73] Assignee: Bunge (Australia) Pty. Ltd., Melbourne, Australia

[ * ] Notice: The portion of the term of this patent subsequent to Jan. 10, 2006 has been disclaimed.

[21] Appl. No.: 154,938

[22] Filed: Feb. 11, 1988

[30] Foreign Application Priority Data

Feb. 20, 1987 [AU] Australia .................................. PI0462

[51] Int. Cl.$^5$ .......................... C07K 15/26; C07K 3/00
[52] U.S. Cl. .................................... 530/351; 435/69.3;
435/69.4; 435/69.51; 435/69.5; 530/408;
530/409; 530/350; 530/399; 530/420; 530/422;
530/423; 530/412; 530/404; 530/405
[58] Field of Search ....................... 435/68, 69.3, 69.4,
435/69.5, 69.51; 530/408, 409, 350, 351, 399,
420, 422, 423, 412, 404, 405

[56] References Cited

U.S. PATENT DOCUMENTS 4,731,440  3/1988  Bentle et al. ........................ 530/399
4,797,474  1/1989  Patroni et al. ...................... 530/351

FOREIGN PATENT DOCUMENTS 0114506  8/1984  European Pat. Off. ........... 435/69.4

OTHER PUBLICATIONS

Osterman, Lev A., *Methods of Protein and Nucleic Acid Research*, vol. 1, Springer-Verlag, New York, 1984.

*Primary Examiner*—Margaret Moskowitz
*Assistant Examiner*—Keith C. Furman
*Attorney, Agent, or Firm*—Merchant, Gould, Smith, Edell, Welter & Schmidt

[57] ABSTRACT

A method for the preparation of proteins in biologically active form including providing a source of protein solubilized from inclusion bodies with a cationic surfactant; providing a weak denaturing agent; and contacting the solubilized protein with the weak denaturant in water in an amount sufficient to allow the protein to remain in a biologically active form.

6 Claims, No Drawings

PRODUCTION OF PROTEINS IN ACTIVE FORMS

BACKGROUND OF THE INVENTION

The present invention relates to a method for the separation of a protein in a biologically active or native form.

Recombinant DNA technology provides potentially extremely valuable means of synthesizing amounts of desirable eukaryotic (usually mammalian) proteins such as hormones, interferons, and enzymes. Although it has proved to be relatively easy to manipulate organisms such as bacteria in order to produce the desired protein, the host organism does not normally secrete the protein product into the culture medium. Thus lysis of the organisms (for example bacteria), followed by isolation of the desired protein is usually necessary.

A protein may exist as a chain of amino acids linked by peptide bonds. In the normal biologically active form of such a protein or its native form as it is referred to, the chain is folded into a thermodynamically preferred three dimensional structure, the conformation of which is maintained by steric interaction and inter- and/or intra-atomic forces such as hydrogen bonding, hydrophobic interactions and charge interactions. In the prior art, the usual aggregation and insolubility under folding conditions of fully, or partially, unfolded proteins requires that folding be carried out in the presence of reducing agents and in very dilute solutions, consequently, in large volumes. The handling of such dilute solutions and large volumes together with toxic reducing agents such as B-mercaptoethanol would add significantly to the cost when such processes are applied industrially.

In copending Australian Patent Application No. 66874/86 applicants have described a method for the recovery of proteins in a soluble form from an insoluble protein source utilising a cationic surfactant. Whilst this process allows for the efficient recovery of proteins in a soluble form, the proteins may not exhibit their normal biological activity. The proteins so recovered may not be in their native form.

Accordingly, it is an object of the present invention to overcome, or at least alleviate, one or more of the difficulties related to prior art.

SUMMARY OF THE INVENTION

Accordingly, in a first aspect, there is provided a method for the preparation of a protein in a physiologically active or native form, which method includes
providing a source of protein in a solubilized form;
and an agent capable of rupturing atomic forces within the molecule, and
contacting the protein with the atomic forces rupturing agent in an amount sufficient to allow the protein to convert to a physiologically active form, which agent is selected from urea, or derivatives thereof, dimethylsulphone, and mixtures thereof.

The source of protein in a solubilized form may be provided by the treatment of the insoluble form with a surfactant. Preferably the surfactant is a cationic surfactant such as described in Australian Patent No. 66874/86, the entire disclosure of which is incorporated herein by reference. The solubilized protein may accordingly be provided from a source of insoluble protein including protein aggregates.

It is particularly preferred, however, that the solubilized protein is formed in a solution wherein the amount of reducing agent is substantially reduced or eliminated.

DETAILED DESCRIPTION OF THE PREFERRED EMBODIMENT

The present invention is particularly applicable to biologically active proteins synthesized by microorganisms and eukaryotic cell lines which have been modified by recombinant DNA technology. The protein aggregate may comprise an inclusion body isolated by disruption or lysis of a host cell which may have been transformed or transfected with a vector including a gene coding for the protein. However it is not restricted thereto. In addition the present invention is applicable to naturally occurring precipitated protein complexes.

Preferably the source of protein in a solubilized form is a source of protein aggregates solubilized with a cationic surfactant.

The protein aggregates which may be recovered according to the present invention may be selected from protein precipitates including inclusion bodies and cytoplasmic aggregates. The inclusion bodies may be selected from biologically active polypeptides and peptides including growth hormones including porcine, bovine and ovine growth hormones, interferons, immunogens and lymphokines. In particular, it has surprisingly been discovered that the solubilized protein aggregates may comprise a solution of crude inclusion bodies which, after solubilization, have been subjected to little or no purification prior to their utilization in the process of the present invention.

For example, crude inclusion bodies including growth hormones in concentrations as low as approximately 13% may successfully be processed utilizing the process of the present invention.

The agent capable of rupturing atomic forces may be an agent capable of either rupturing hydrogen bonds, hydrophobic interactions or charge interactions. The agent capable of rupturing atomic forces may be selected to be sufficiently mild to allow other appropriate atomic forces to reform. The agent may be selected from urea, or derivatives thereof including dimethylhydroxy urea and dimethylsulphone and mixtures thereof. The agent may be provided in a suitable aqueous solution. A solution including a polar organic solvent may be used. Acetonitrile, acetic acid or dimethyl sulphone may be used.

The source of protein in a solubilized form may be contacted with the solution of the atomic force rupturing agent in any suitable manner. If desired the source of protein may be precipitated out of solution. The precipitate may then be mixed with the rupturing agent solution. However, it is not necessary to include a precipitation step. For example, the source of protein in a solubilized form may be dialyzed or exchanged into a solution of the atomic force rupturing agent. The source of protein may be utilized in a concentrated form. The source of protein may be present in an amount of approximately 1 to 200 mg/ml.

In a preferred aspect the method according to the present invention further includes the step of contacting the physiologically active protein with a physiologically acceptable solvent.

The physiologically acceptable solvent may be water or other dilute aqueous solution. A buffered aqueous solution is preferred. It has been found, surprisingly, that after the treatment according to the method of the present invention, the solubilized protein is rendered soluble in aqueous solution and is converted into its biologically active form. Preferably, the pH of the solution is optimized to ensure solubility of the protein and stability of the solution. For example when the physiologically active protein is a growth hormone, the pH is maintained between approximately 8.5 and 11.0.

The atomic force rupturing agent may be utilized in any suitable amount. We have surprisingly found that relatively low concentrations of the atomic force rupturing agent are effective in the method according to the present invention. Where the rupturing agent is selected from urea, derivatives thereof and dimethylsulphones, the atomic force rupturing agent may be used in concentrations of from approximately 0.5 M to 8 M, preferably betwen approximately 3 to 5 M.

The method may be conducted at any suitable temperature above the freezing point of the solution. Preferably a temperature in the range of approximately 4 to 25° C. more preferably 4° to 10° C. may be used. At such relatively low temperatures an improved yield may be achieved.

Further, in contrast to the prior art, we have surprisingly found that the contact step in the method for the preparation of protein in a physiologically active form according to the present invention may be conducted with solutions free or substantially free from reducing agents. More surprisingly, we have found that the amount of reducing agent may be substantially reduced or omitted also from the solubilization step. For example, in examples 1 and 2 below the amount of dithiothreitol in the solubilization step and the amount of mercaptoethanol in the contact step may be reduced or eliminated.

In the method for the recovery of proteins in a solubilized form, utilising a surfactant, e.g. as described in Australian Patent Application No. 66874/86 it is preferred that the solubilized protein be separated from the resulting solution. The purification step may be selected from differential elution of the solubilized protein through a chromatographic support, dialysis, ultrafiltration, differential precipitation, or ligand specific isolation. Whilst such a separation step may be used in conjunction with the method according to the present invention it has surprisingly been found that such a separation step is not required to produce a physiologically active preparation.

The present invention will now be more fully described with reference to the accompanying examples. It should be understood, however, that the description following is illustrative only and should not be taken in any way as a restriction on the generality of the invention described above.

EXAMPLE 1

Size Exclusion Chromatography

An experiment was conducted with crude inclusion bodies obtained from transformed *E.coli* cells. The inclusion bodies, containing 1-190AA methionine-porcine growth hormone, derived from plasmid, pMG935, were isolated, after cell disruption, by centrifugation. The insoluble pellet (100 g wet weight) was washed three times with an aqueous solution containing 5% Triton X-100 and 5 mM EDTA and then three times with water containing 5 mM EDTA. The pellet was recovered at each step by centrifugation (25,000 g). The final pellet was resuspended and vigorously agitated with an aqueous solution of cetyltrimethylammonium bromide (100 ml of 18.5% w/v), 0.15 M TRIZMA (pH 9.0), 50 mM EDTA and dithiothreitol (5% w/v). After 1 hour the mixture was centrifuged (25,000 g, 30 min.), the clear supernatant retained and the pellet resuspended in 100 ml of the fresh solubilizing buffer. Following collection of the final supernatant the pellet was discarded and the combined supernatant loaded onto a column (75 cm×11 cm) packed with Sephacryl S300 which had previously been equilibrated with eluant consisting of a solution of cetyltrimethylammonium bromide (0.36%), 30 mM TRIZMA (pH 10.0) and dithiothreitol (0.5% w/v).

Elution of the column followed at a flow rate of 11 ml/min. After collection of some 8L of eluant the fraction containing the growth hormone was isolated in some 600 ml of eluant. This fraction was then diluted approximately 1:10 with water to give a UV (280 nm) absorbance of 1.5, and the solution placed into cellulose dialysis sacks (Union Carbide type 30), and placed into exchange buffer containing 5 M urea, 0.05 M glycine (pH 11.0) and B-mercaptoethanol (0.1%) sufficient to provide an estimated 1:160,000 dilution of the initial solubilizing buffer contained within the dialysis sack.

The dialysis sacks were then placed into a physiologically compatible exchange buffer consisting of mannitol (1% w/v), 0.05 M glycine (pH 10.0) without exclusion of air at room temperature. The buffer was exchanged at 8 hourly intervals with fresh buffer sufficient to provide a 1:160,000 dilution of the urea solution.

This final product was then tested for biological activity in rats according to the rat tibia assay, and was found to be active compared to a positive control containing native porcine growth hormone extracted from fresh pituitaries (see Table 1).

EXAMPLE 2

Experiments paralleling those described in Example 1 were conducted with inclusion bodies containing 4-190AA porcine growth hormone derived from plasmid pMG 936 in *E.coli*.

The experiment used inclusion bodies containing 4-190AA porcine growth hormone (100 g wet wt) isolated in the same manner as that described for 1-190AA methionine porcine growth hormone inclusion bodies. The inclusion body paste was vigorously agitated with an aqueous solution with cetyltrimethylammonium chloride (200 ml of 18.5% w/v, 25° C.) 0.15 M TRIZMA (pH 10.0), 50 mM EDTA and dithiothrietol (3% w/v). After 1 hr the mixture was diluted with water (80 ml) and clarified by filtration through a pad of diatomaceous earth. The clear filtrate was loaded onto a column (75 cm×11 cm) packed with Sephacryl S300 which had previously been equilibrated with eluant consisting of an aqueous solution of cetyltrimethylammonium chloride (0.35% w.v), 30 mM TRIZMA (pH 10.0) and dithiothreitol (0.5% w/v).

Elution of the column followed at a mean flow rate of 11 ml/min. After collection of some 10 L of eluant the fraction containing the growth hormone was isolated in some 800 ml of eluant. The fraction after dilution with eluant buffer, approximately 1:10, gave a UV (280 nm) absorbance of 0.8. The fraction was placed into cellulose dialysis sacks and exchanged into 1,3 bis (hydroxymethyl) urea (3.5 M) 0.05 M glycine (pH 11.0) sufficient to provide a 1:160,000 dilution of microsolutes contained within the sacks.

The dialysis sacks were then placed into physiologically compatible exchange buffer consisting of mannitol (1% w/v), 0.05 M TRIZMA (pH 10.0) without exclusion of air at 5° C. The buffer was exchanged at 8 hourly intervals with fresh buffer sufficient to provide a 160,000 dilution of microsolutes in the sacks.

This final product was found to be active when tested for biological activity in rats in a similar manner to that described in Example 1.

EXAMPLE 3

(a) In the Presence of Reducing Agent

The fraction (600 ml) containing growth hormone isolated by size exclusion chromatography, as described above in Example 1, was placed directly into an Amicon CH2A concentrator equipped with a S1 Y10 cartridge and the solution continuously exchanged by dialysis with a fresh buffer containing 5 M urea, 0.05 M glycine (pH 11.0) and 0.1% B-mercaptoethanol. Sufficient exchange buffer was used to provide a 1:160,000 dilution of the initial microsolutes. The resulting solution was subsequently exchanged in a similar manner into a physiologically compatible aqueous buffer containing mannitol (1%) and 0.05 M glycine (pH 10.0) without exclusion of air at room temperature. This final product was found to be active compared to a positive control containing native porcine growth hormone according to the rat tibia assay (see Table 1).

(b) In the Absence of Reducing Agent

The fraction (600 ml) containing growth hormone isolated by size exclusion chromatography, as described above in Example 1, was placed directly into an Amicon CH2A concentrator equipped with a S1 Y10 cartridge and the solution continuously exchanged by dialysis with a fresh buffer consisting only of 5 M urea, 0.05 M glycine (pH 11.0). The urea solution was then similarly exchanged into an aqueous solution of mannitol (1%), (w/v) and 0.05 M glycine (pH 10.0).

In both dialysis steps sufficient exchange buffer was used to provide a 1:160,000 dilution of the microsolutes. The final product was found to be highly soluble in physiologically acceptable buffer and shown to be biologically active by the rat tibia assay (see Table 1).

EXAMPLE 4

Crude Inclusion Bodies

Another experiment was conducted beginning with crude inclusion bodies (50 mg) containing 4-190AA synthetic porcine growth hormone, previously washed three times with an aqueous solution containing 5% Triton X-100 and 5 mM EDTA and then three times with an aqueous 5 mM EDTA. The inclusion bodies were vigorously agitated with an aqueous solution of cetyltrimethylammonium bromide (1 ml of 10.5% w/v), 0.15 M TRIZMA (pH 10.0) 50 mM EDTA and dithiothreitol (5% w/v). After 1 hour the mixture was centrifuged (25,000 g, 30 min). The clear supernatant was then diluted with approximately 1:50 with water to give a UV (280 nm) absorbance of 1.5 and the clarified solution placed into dialysis sacks (Union Carbide Type 30) and dialyzed against exchange buffer containing 7 M urea, 0.05 M glycine (pH 11.0); sufficient exchange buffer was used to provide a dilution of 1:160,000 of initial microsolutes. The dialysis sacks containing 7 M urea were then placed into a physiologically acceptable exchange buffer consisting of 0.05 M glycine (pH 10.0), without exclusion of air at room temperature, and the process of dialysis continued until a dilution of 1:160,000 of initial microsolutes was achieved.

The final solution was then found to have biological activity when compared to a positive control comprising a preparation of native porcine growth hormone extracted from fresh pituitaries (see Table 1).

EXAMPLE 5

An experiment was conducted with crude inclusion bodies (50 mg) containing the D1 fragment of the 32 kDa structural protein from infectious bursal disease virus which had previously been sequentially washed (x3) with aqueous Triton X-100 (5%), 5 mM EDTA and aqueous 5 mM EDTA. The inclusion bodies were vigorously agitated with an aqueous solution containing a mixture of cetyltrimethylammonium bromide (0.5 ml of 18.5% w/v) and cetylpyridinium chloride monohydrate (0.5 m of 12% w/v), 0.15 M TRIZMA (pH 10.0), 50 mM EDTA and dithiothreitol (5% w/v). After 1 hour the mixture was centrifuged (25,000 g 30 min.). The clear supernatant was then diluted approximately 1:30 with 5 M urea and the solution placed into dialysis sacks and dialyzed against exchange buffer containing 5 M urea, 0.05 M glycine (pH 11.0), sufficient exchange buffer was used to provide a dilution of approximately 1:160,000 of initial microsolutes. The dialysis sacks were then placed into a physiologically acceptable exchange buffer consisting of mannitol (1% w/v), 0.05 M TRIZMA (pH 10.0) without the exclusion of air at room temperature. The process of dialysis was continued until a dilution of approximately 1:160,000 of initial microsolutes was achieved.

An immuno-dot blot analysis of the final solution using nitro-cellulose paper and a monoclonal antibody to the D1 polypeptide confirmed the antigenicity of the fused polypeptide.

EXAMPLE 6

An experiment was conducted with washed inclusion bodies containing 1-190AA methionine-porcine growth hormone. The inclusion bodies (50 mg) were vigorously aggitated (1 hr) with a solution of acetonitrile (0.2 ml), aqueous buffer (0.1 M glycine, pH 8.5; 0.8 ml) and aqueous cetyltrimethylammonium bromide (0.5 ml of 30% w/v) and dithiothreitol (3% w/v) in a test tube at 25° C. The mixture was then centrifuged (25,000 g, 20 min.) to give a clear supernatant. The supernatant was then diluted approximately 1:3 with a 1:1 mixture of 2 M urea and 2 M dimethylsulphone and placed into dialysis sacks. The mixture was dialysed against a solution of 2 M urea and 2 M dimethylsulphone (1:1) until a dilution of initial microsolutes of 1:160,000 had been achieved. The dialysis sacks were then placed into a physiologically compatible buffer consisting of aqueous 0.05 M TRIZMA (pH 10.0) and NaCl (0.8%) without the exclusion of air and dialysis was continued to give a dilution of microsolutes of 1:160,000.

A test for biological activity of the final solution by the rat tibia assay proved positive when compared to a positive control containing naturally derived porcine growth hormone.

EXAMPLE 7

An experiment was conducted with washed inclusion bodies containing 1-190AA methionine-porcine growth hormone. The inclusion bodies (50 mg wet wt) were vigorously aggitated (1 hr) with a solution of cetyltrimethylammonium bromide (1.0 ml of 18.5% w.v), 0.15 M TRIZMA (pH 10.0) and 50 mM EDTA. After 1 hr the mixture was centrifuged (25,000 g, 30 min). The clear supernatant was then diluted approximately 1:50 with water to give a UV (280 nm) absorbance of 1.2 and the clarified solution placed into dialysis sacks (Union Carbide Type 30) and the solution exchanged against 7 M urea, 0.05 M glycine (pH 11.0), sufficient to provide a dilution of microsolutes by approximately 1:160,000. The dialysis sacks were then placed into a physiologically acceptable buffer consisting of 0.05 M TRIZMA (pH 9.5) at 4° C. without the exclusion of air and the process of dialysis continued until a dilution of approximately 1:160,000 of initial microsolutes was achieved.

The final solution was then found to have biological activity when compared to a positive control (see Table 1).

| Treatment Group | *Biological Activity (%) |
| --- | --- |
| Example 1 | 38 |
| Example 3a | 30 |
| Example 3b | 34 |
| Example 4 | 19 |
| Example 7 | 25 |

Finally, it is to be understood that various other modifications and/or alterations may be made without departing from the spirit of the present invention as outlined herein.

We claim:

1. A method for the preparation of a protein in a biologically active form comprising:

solubilizing a water-insoluble protein, obtained from inclusion bodies, with an aqueous cationic surfactant to form a first protein solution, said protein being selected from the group consisting of physiologically active polypeptides, growth hormones, interferons, immunogens and lymphokines;

exchanging the solvent of the first protein solution for a biologically acceptable solvent selected from the group consisting of water, dilute aqueous solutions and buffer to form a second protein solution in which the protein refolds to its biologically active form, said biologically acceptable solvent being free of denaturants and surfactants; and contacting said second protein solution with an aqueous mixture of a weak denaturing agent selected from the group consisting of urea, dimethylsulphone and mixtures thereof in an amount sufficient to substantially prevent the precipitation of the protein, thereby allowing the protein in the solution to maintain its biologically active form.

2. A method according to claim 1 wherein said solubilized protein is contacted with said weak denaturing agent in a solution free from reducing agents.

3. A method according to claim 1 wherein said inclusion bodies are crude inclusion bodies.

4. A method according to claim 1 wherein said weak denaturing agent is present in concentrations of from approximately 0.5 M to 8 M.

5. A method according to claim 4 wherein the pH of the solution so formed is optimized to ensure solubility of the protein.

6. A method according to claim 5 wherein, when said biologically active protein is a growth hormone, the pH is maintained between approximately 8.5 and 11.0.

* * * * *

UNITED STATES PATENT AND TRADEMARK OFFICE
CERTIFICATE OF CORRECTION

PATENT NO. : 4,966,963

DATED : October 30, 1990

INVENTOR(S) : Joseph J. Patroni

It is certified that error appears in the above-identified patent and that said Letters Patent is hereby corrected as shown below:

Column 5, line 6, for "160,000" it should read --1:160,000--; and

Column 7, line 19, insert

--TABLE 1

The *biological activity of preparations described above, as assessed by the rat tibia assay, relative to an equivalent dose of porcine growth hormone isolated from pituitaries as positive control (assessed as 100 $\pm$ 10%). --

Signed and Sealed this

Nineteenth Day of May, 1992

*Attest:*

DOUGLAS B. COMER

*Attesting Officer*     *Acting Commissioner of Patents and Trademarks*